United States Patent [19]

Schwyn

[11] Patent Number: Plant 7,270

[45] Date of Patent: Jul. 17, 1990

[54] FUCHSIA×HYBRIDA CV. ISLAND SUNSET

[75] Inventor: Geoff Schwyn, Delta, Canada

[73] Assignee: Monrovia Nursery Company, Azusa, Calif.

[21] Appl. No.: 238,280

[22] Filed: Aug. 30, 1988

[51] Int. Cl.[5] ..... A01H 5/00
[52] U.S. Cl. ..... Plt./68
[58] Field of Search ..... Plt. 68

*Primary Examiner*—James R. Feyrer

[57] ABSTRACT

A new and distinct selection of Fuchsia×hybrida *HORT ex VILM.* shrub (popularly known as Fuchsia) which shall be referred to hereinafter as Fuchsia×hybrida cv. Island Sunset. Fuchsia×hybrida cultivar Island Sunset differs distinctively from other Fuchsia plants by a unique combination of multi-colored foliage, red and purple flowers and cold hardiness.

DISCOVERY

This invention relates to a new and distinct selection of Fuchsia×hybrida, a member of the Onagraceae or evening primrose family. Fuchsia×hybrida cv. Island Sunset was discovered by me in a garden in Richmond, British Columbia in the Spring of 1984.

REPRODUCTION

My new selection has been strictly asexually reproduced by cuttings at Westham Island Nursery and Monrovia Nursery Company. The distinct phenotypic characteristics of this new selection that set this plant apart from other Fuchsia plants could be lost genetically through sexual reproduction. Therefore, sexual reproduction is prohibited and propagation is restricted to asexual reproduction by cuttings. Seed progeny from the new selection has not been observed.

1 Drawing Sheet

BRIEF DESCRIPTION OF THE DRAWINGS

The accompanying illustrations show a typical specimen of the plant according to this invention and are depicted in color as nearly true as possible.

DESCRIPTION

Figure 2:
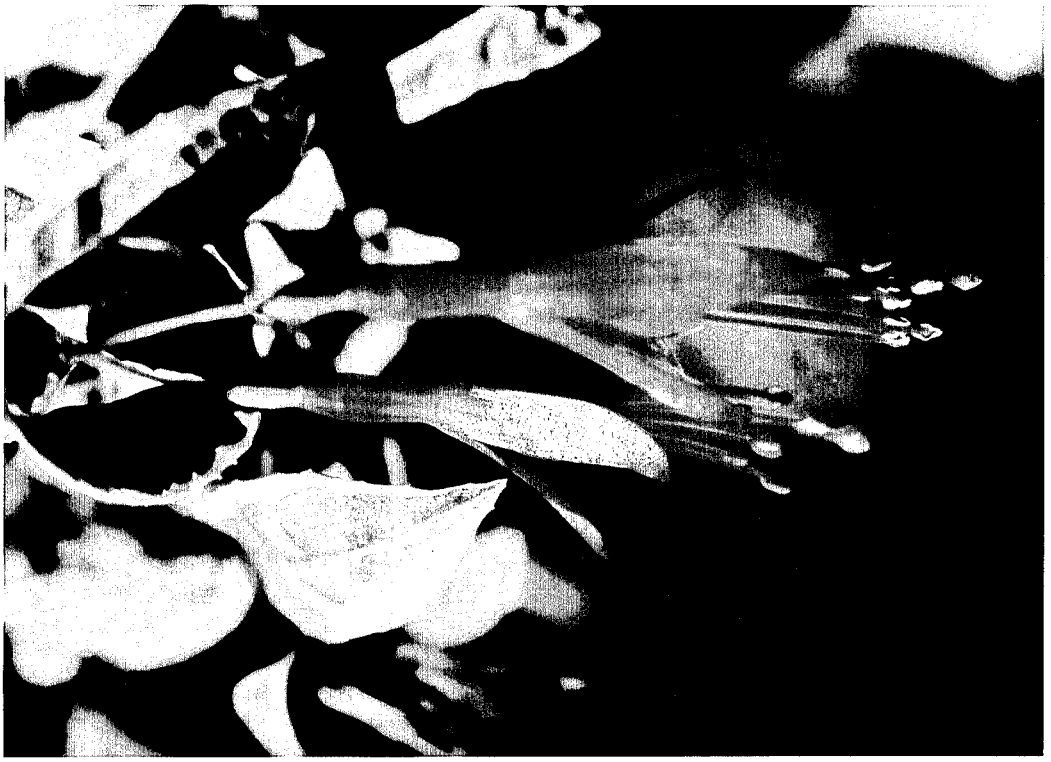
FIG. 2, depicts a close up of the slender drooping purple and red flowers.
Figure 1:
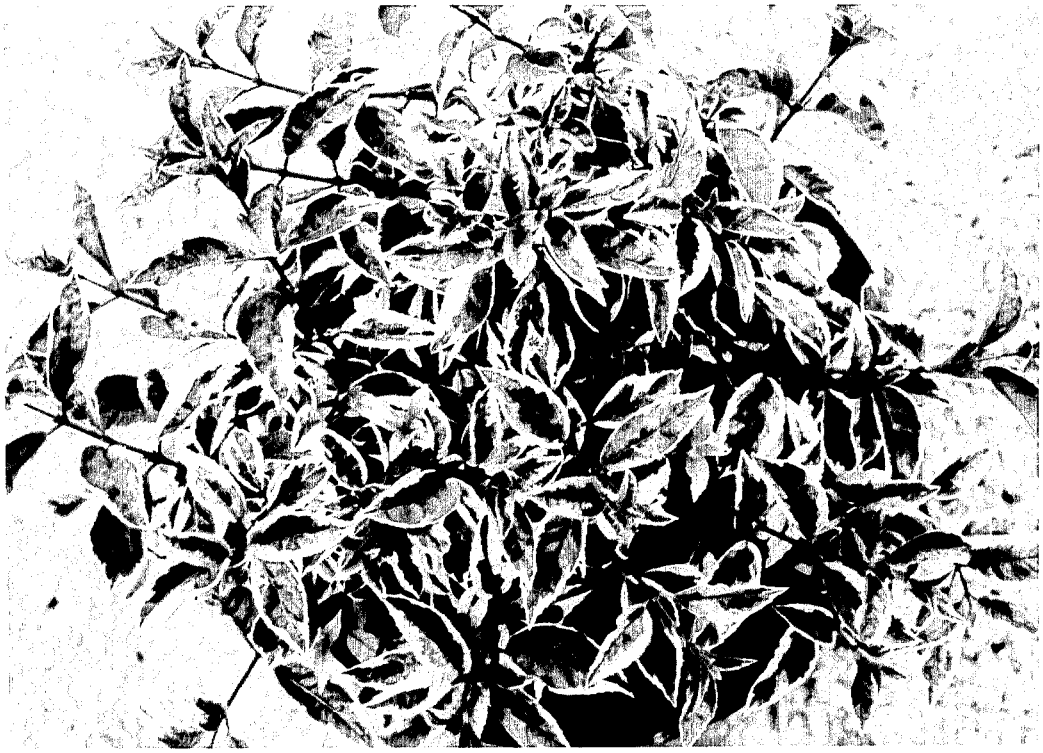
FIG. 1, shows the overall growth habit and the attractive multicolored foliage, the new red foliage changing to pink is also to be noted.

Below is a detailed description of the new Fuchsia×hybrida cv. Island Sunset, the color terminology is from the British Horticultural Color Charts.

Overall size and havit: Evergreen foliage with a stiff spreading and trailing habit. The plant is always wider than tall, after 2 years the height is 2 feet with a spread of 3½ feet.

Flower: Floriferous habit, in the Pacific Northwest the blooming period is mid July through October (or frost)

*Size at flowering.*—Length: Including ovary and tube 4.5 cm (+ or −2 mm). Width: At widest portion 2.2 cm (+ or −2 mm).

*Sepals.*—4 in number, tip recurved. Length: 1.3 cm to 2.5 cm. Width: 0.4 cm to 0.7 cm. Color: 022 Rose Opal.

*Tube.*—Color 022 Rose Opal.

*Corolla.*—4 in number. Length: 1.6 cm. Width: 1.5 cm. Shape: Obovate. Color: 733 Violet Purple. Base: 022 Rose Opal.

*Stamens.*—8 in number. Extending beyond corolla 1.0–2.2 cm in length.

*Pistil.*—Extending beyond corolla 2.2–3.2 cm in length.

*Bud.*—Narrow elliptic in shape.

Foliage:

*Size.*—Width 2.5–3 cm; length 5.5–6 cm.

*Shape.*—Narrowly ovate-lanceolate.

*Base.*—Obtuse.

*Tip.*—Acuminate.

*Color.*—Spinach Green 0960/1. Margins: mature growth: uranium green 63/3. Juvenile growth: uranium green 63/2. New growth: Fuchsia Purple 28 with tones of Rose Opal 022/1.

*Margins.*—Slightly serrate.

*Arrangement.*—Opposite, decussate.

*Pubescence.*—Both surfaces glabrous.

*Pentiole.*—0.5 to 1 cm in length.

*Cold hardiness.*—Root hardy with a mulch cover to 0° F.

I claim:

1. A new and distinct selection of Fuchsia×hybrida as substantially shown and described herein, that is characterized particularly as a novelty by the unique combination of multi-colored foliage, red and purple flowers and cold hardiness.

* * * * *